United States Patent [19]

Crowe et al.

[11] Patent Number: 4,705,783

[45] Date of Patent: Nov. 10, 1987

[54] 9ALPHA, 11BETA-SUBSTITUTED AND 11BETA-SUBSTITUTED ESTRANES

[75] Inventors: David F. Crowe, Yreka; Masato Tanabe, Palo Alto; Richard Peters, San Jose, all of Calif.

[73] Assignee: SRI International, Menlo Park, Calif.

[21] Appl. No.: 748,489

[22] Filed: Jun. 25, 1985

[51] Int. Cl.$^4$ .................. A61K 31/56; C07J 00/00
[52] U.S. Cl. ................. 514/180; 260/397.45; 260/397.5; 514/179; 514/182
[58] Field of Search ............... 260/397.45, 397.5; 514/179, 180, 182

[56] References Cited

U.S. PATENT DOCUMENTS

| | | | |
|---|---|---|---|
| 3,755,574 | 8/1973 | Bertin et al. | 514/182 |
| 3,980,681 | 9/1976 | Sykes et al. | 260/397.45 |
| 4,312,864 | 1/1982 | Tax | 260/397.5 |

FOREIGN PATENT DOCUMENTS

| | | |
|---|---|---|
| 2752695 | of 1978 | Fed. Rep. of Germany . |
| 1453216 | of 1966 | France . |
| M6854 | of 1969 | France . |
| 1151404 | of 1969 | United Kingdom . |

OTHER PUBLICATIONS

Chemical Abstracts; vol. 75 (1971) #129995F; Sykes et al.

Chemical Abstracts; vol. 75 (1971) #88842H; Sykes et al.

*Tetrahedron Letters*, P. J. Sykes, "Oxidation Of Ring A–Aromatic Steroids To 9,11/3–Diol 11–Nitrates With Ceric Ammonium Nitrate" No. 37, Sep. 1971, pp. 3393–3395.

*Steroids*, vol. 34, No. 4. Oct. 1979, J. Salmon et al., "Reference Compounds For The Study Of Moxestrol Metabolism" pp. 381–400.

*Chemical Abstracts*, vol. 100, No. 15, Apr. 1984, Li, Zhensu et al., "Synthesis of 11-Substituted (Containing Oxygen Group) Estradiol), p. 626, Abstract No. 121429p.

*Journal of Medicinal Chemistry*, vol. 10, No. 6, Nov. 1967, J. S. Baran, "A Synthesis Of 11beta–Hydroxyestrone And Related 16–and 17–Hydroxyestratrienes", pp. 1188–1190.

J. P. Raynaud, et al.; *Drug Design*, vol. VIII, 1979, pp. 178–181.

*Primary Examiner*—Douglas W. Robinson
*Attorney, Agent, or Firm*—Ciotti & Murashige, Irell & Manella

[57] ABSTRACT

9 alpha, 11 beta and 11 beta-substituted estranes are disclosed which exhibit elevated estrogenic and postcoital contraceptive activities. A process for their manufacture and their use in pharmaceuticals is also disclosed.

34 Claims, No Drawings

9α, 11β-SUBSTITUTED AND 11β-SUBSTITUTED ESTRANES

ORIGIN OF THE INVENTION

This invention was made in performance of a United States government contract, No. NO1-HD-5-2844 issued by the National Institutes of Health.

BACKGROUND OF THE INVENTION

1. Field of the Invention

This invention concerns 9α,11β- and 11β-substituted estranes and their manufacture and their uses as active estrogenic and postcoital contraceptive agents.

2. General Background and Prior Art

It has long been recognized that estrogenic hormones are important pharmacologial materials which find a wide range of beneficial applications in human and veterinary therapy. Such applications include, for example, supplementing the estrogen levels in persons in need of the same; incorporation into birth control devices and compositions; and the like. Of the available natural and synthetic estrogens, estradiol has been among the most studied and is among the most active. Estradiol preparations are marketed commercially such as the product sold under the tradename Estrace. Estradiol is not orally active and must be administered parenterally.

It has also been long recognized that estrogens which are orally active are very attractive because of the obvious advantages of nontraumatic oral administration. In the late 1930's, Inhoffen et al described ethynyl estradiol (19-Nor-17A-pregna-1,3,5(10)triene-20-yne-3,17-diol.

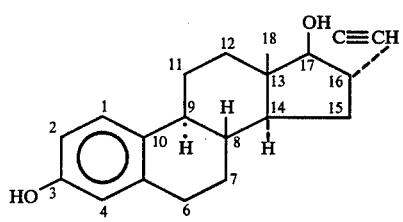

Naturwiss, 26, 96 (1938). This material is noted in such other early references as Inhoffen, et al. Ber. 71, 1024 (1938); German Pat. No. 702,063; British Pat. No. 516,444; and U.S. Pat. Nos. 2,243,887; 2,251,939; 2,265,976; and 2,267,257. As early as 1951, (Petit et al. Bull. Soc. Chim. France, 1951, 121) it was recognized that the material produced estrogenic effects in mammals when administered orally. This had led to its wide adoption as an oral estrogen and its marketing in a range of products and dosage forms under such proprietary names as, for example, Diogyn-E, Dyloform, Etinestryl, Ethidol, Estinyl, Etivex, Feminone, Inestra, Kolpolyn, Linoral, Lynoral, Novestrol, Oradiol, Orestralyn, Primogyn, and Progynon.

Ethynyl estradiol is also widely employed together with progestins such as norethindrone and noresthindrone acetate in oral contraceptives to give products substantially superior in effectiveness to materials without ethynyl estradiol. Examples of these ethynyl estradiol-containing contraceptive products include materials marketed under the proprietary names of Brevicon, Demulen, Loestrin, Modicon, Norinyl, Ortho-Novum, Ovcon, Oural, and Tri-Norinyl.

While the advantages of estradiol and ethynyl estradiol are substantial, as evidenced by their wide commercial adoption, these products are not without their drawbacks. These problems are extremely serious when viewed in terms of the large number of women who take preparations such as those listed above on a long and regular basis. These problems include enhancing the risk of endometrial carcinoma; induction of malignant carcinoma especially in the cervix, breast, vagina and liver; promotion of gallbladder disease, thromboembolic and thrombotic diseases, myocardial infarction, hepatic adenoma, elevated blood pressure, and hypercalcemia; and a worsening of glucose tolerance. These problems tend to manifest themselves at the dosage levels needed to achieve the desired primary estrogenic and contraceptive effects. Many of these side effects are considered to be dose-related. If more potent oral estrogens were available, they could be used in lower doses and the side effects could, at least in part, be reduced or eliminated.

The present invention provides a family of such more active estrogens. The following publications and United States Patent are believed to be of interest to these new materials and their preparation: P. J. Sykes and F. J. Rutherford, Tet. Lett. 37, 3393, (1971); K. Tsuda, S. Nozoe and Y. Okada, Chem. Parm. Bull. 11, (8), 1022, (1963); B. Magerlein and J. Hogg, J. Am. Chem. Soc. 80 2220 (1958); J. Baran, J. Med. Chem. 10, 1188, (1967); and U.S. Pat. No. 3,755,574, issued Aug. 28, 1973. In comparison to the disclosures of these references, the present invention provides materials not shown by them and provides easier access to the general class of 11β and 9α,11β-substituted estranes not previously available.

It is important to recognize that, notwithstanding the large volume of effort that has been devoted to research into the preparation and production and the testing of synthetic and naturally occurring steroids such as the estrogens, this is still very much an empirical field. Simple or seemingly insignificant shifts in one or two atoms or groups in a steroid can render a new compound active or inactive or change dramatically the entire character of its activity.

STATEMENT OF THE INVENTION

We have now discovered that certain 11β and 9α,11β-substituted derivatives of estradiol, and in some instances in particular of ethynyl estradiol, offer estrogenic activity and postcoital contraceptive activity which is in many cases many times greater than that obtained with nonderivatized material. Thus, the present invention in one aspect provides these derivatized analogues of estradiol and ethynyl estradiol as new chemical compounds having the chemical formula

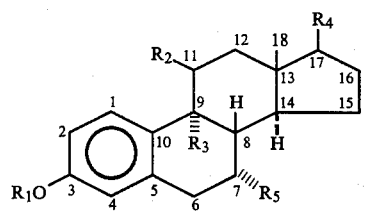

In this formula, $R_1$ is hydrogen, a lower alkyl or cycloalkyl or a lower acyl; $R_2$ is a nitrate, a halo, a lower alkyl or a hydroxyl; $R_3$ is hydrogen, hydroxyl or a lower alkoxy; $R_4$ is either a carbonyl oxygen or is a pair of groups, the alpha position one of which is hydrogen or a lower alkynyl and the beta one of which is hydroxyl, a lower alkyl or a N alkanoic acid ester; and $R_5$ is hydrogen or a lower alkyl. When $R_2$ is nitrate, $R_3$ is hydroxyl, and $R_4$ is carbonyl, $R_5$ must be a lower alkyl. When $R_2$ is a halo $R_3$ must be hydrogen. When $R_2$ is hydroxyl $R_5$ must be a lower alkyl. In other aspects this invention provides new estrogenic and postcoital contraceptive pharmaceutical preparations containing effective dosing amounts of these compounds and unit dosage forms thereof. In this aspect, the invention molecules provide the use of an additional material wherein $R_1$ is lower acyl, $R_2$ is nitrate, $R_3$ is hydroxyl, $R_4$ is a carboxyl carbon and $R_5$ is hydrogen. This material is shown by Sikes above but its use in such pharmaceutical products is believed new. In yet another aspect the present invention provides methods of treatment to obtain estrogenic and postcoital contraceptive effects in a mammal by administering to said mammal an effective dose of the compounds (or more commonly the pharmaceutical preparations) of the invention. In a yet further aspect, this invention provides a process for introducing substituents into the 11β and the 9α positions in an estrane, which process has the steps of first treating an R1, R4 and R5-substituted estrane with about four equivalents of ceric ammonium nitrate and $R_2$- and $R_3$-inserting nucleophiles. This can insert nitrate, halo or alkoxy $R_2$ groups and hydroxy or alkoxy $R_3$ groups into the structure.

The same insertions can be accomplished starting with the Δ9,11 equivalent starting steroid and using 2 equivalents of ceric ammonium nitrate in place of 4 equivalents of ceric ammonium nitrate. The $R_3$ group can be removed by treatment with a silane followed by $BF_3$ in ether. An $R_2$ nitro group can be converted to hydroxyl by reduction using a zinc catalyst. This reduction can also be carried out prior to removal of the $R_3$ group in which case the final product has OH's as $R_2$ and as $R_3$.

DETAILED DESCRIPTION OF THE INVENTION

In this specification and in the claims which follow it reference will be made to a number of terms which shall be defined to have the following meanings:

"lower alkyl" means a branched or unbranched saturated hydrocarbon group of one to four carbon atoms such as, methyl, ethyl, i-propyl and n-butyl and the like. For use herein, methyl and ethyl are preferred "lower alkyls" with methyl in general being the more preferred.

"cycloalkyl" means a cyclic saturated hydrocarbon group of four to seven carbon atoms such as cyclobutyl, cyclopentyl, cyclohexyl and cycloheptyl.

"lower acyl" means an R—CO— group wherein R is a lower alkyl of one to three carbon atoms such that the acyl contains a total of from two to four carbon atoms. Of the lower acyls, $CH_3$—CO— (acetyl) is preferred.

"lower alkoxy" means an R—O— group wherein R is a lower alkyl as defined above. Of the lower alkoxies, those having one or two carbon atoms are preferred with one carbon alkoxies (methoxy) being more preferred.

"halo" and "halogen" mean a fluoro, chloro, bromo, or iodo substituent in an organic molecule. Of the halos, chloro and bromo are generally preferred with chloro generally being the more preferred.

"lower alkynyl" means a linear or branched hydrocarbon chain containing from two to four carbon atoms, between two of which is a carbon-carbon acetylenic triple bond. Ethynyl and prop-2-ynyl are representative lower alkynyls with ethynyl being the preferred species.

"alkanoic acid ester" means a group of the formula R—COO—, wherein R is a one to seven carbon atom alkyl. Such esters include, for example, acetate, propionate, butyrate, enanthate and the like. The acetic acid ester, $CH_3$—COO— is generally preferred.

"carbonyl oxygen" means an oxygen atom attached to a carbon atom through a C=O bond.

In describing the location of groups and substituents on the estradiol and ethynyl estradiol rings, the following numbering system will be employed.

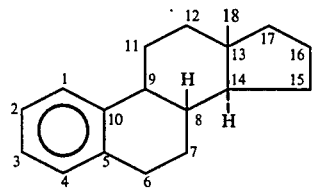

In these structures, the use of solid and dashed lines to denote particular conformation of groups follows the IUPAC steroid-naming convention.

In the compounds of the invention which are set forth in the structural formula given in the Statement of the Invention, $R_1$ may be hydrogen, lower alkyl cycloalkyl or lower acyl. Although not known with certainty, it is believed that the latter two groups undergo cleavage in use of the body so that all of these $R_1$ groups are essentially equivalent from an activity point of view. $R_1$ groups that are preferred because of their simplicity are H—, $CH_3$— and $CH_3$—CO—.

$R_2$ can be nitro, halo, lower alkoxy or hydroxyl. Among the halos, Cl, Br, and F are preferred with Br and Cl being more preferred. Among the lower alkoxies, methoxy is preferred.

$R_3$ can be hydrogen, hydroxyl or a lower alkoxy. (As above, methoxy is the preferred alkoxy.)

$R_4$ represents two bonds. These can be present as a single carbonyl oxygen or they can go to two groups which are arrayed in an alpha and beta configuration. The alpha group may be hydrogen or a lower alkynyl, especially ethynyl. The beta group may be hydroxyl, a lower alkyl or an alkanoic acid ester. A consideration regarding the choice of $R_4$ is that the alkynyl alpha substituent may enhance the oral activity of the product significantly. Importantly, however, with some of the compounds of this invention unexpected significant oral activities (in some cases 7 to 15 times that of ethynyl estradiol) are noted with materials having a carbonyl oxygen $R_4$ and with molecules having a beta hydroxyl $R_4$.

$R_5$ is a lower alkyl or a hydrogen.

The selection of each of $R_1$, $R_2$, $R_3$, $R_4$, and $R_5$ is not made entirely independently of one another. For example, when $R_2$ is nitro, and $R_3$ is OH and $R_4$ is a carbonyl oxygen, $R_5$ should be a lower alkyl. Similarly, when $R_2$ is a halo, $R_3$ should be hydrogen and when $R_2$ is hydroxyl, $R_5$ should be a lower alkyl to fall within the scope of this invention.

As a general class, the compounds having a nitrate $R_2$ are preferred. Special preference is given to the compounds set forth in Table 1. In this table the compounds are identified by listing their $R_1$ through $R_5$ substituents.

TABLE 1

| Compound Identification No.* | $R_1$ | $R_2$ | $R_3$ | $R_4$ | $R_5$ |
|---|---|---|---|---|---|
| 1 | Ac** | —ONO$_2$ | OH | =O | CH$_3$ |
| 3 | Ac | —ONO$_2$ | OH | αC≡C βOAc | H |
| 4 | Ac | —ONO$_2$ | OH | αH β ethyl | H |
| 5 | Ac | —ONO$_2$ | OH | αH β ethyl | CH$_3$ |
| 6 | Ac | —ONO$_2$ | H | =O | CH$_3$ |
| 8 | H | —ONO$_2$ | H | αH β OH | CH$_3$ |
| 7 | Ac | —ONO$_2$ | H | =O | H |
| 10 | Ac | —ONO$_2$ | OCH$_3$ | =O | H |
| 17 | CH$_3$ | Cl | H | αC≡C β OH | H |
| 18 | CH$_3$ | Cl | H | α H β ethyl | H |
| 11 | Ac | Cl | H | =O | H |
| 12 | H | OH | OH | αC≡C | CH$_3$ |
| 13 | Ac | OH | OH | =O | CH$_3$ |
| 14 | Ac | OH | H | =O | CH$_3$ |
| 9 | Ac | OCH$_3$ | OCH$_3$ | =O | H |
| 15 | Ac | OCH$_3$ | H | =O | H |
| 16 | CH$_3$ | OCH$_3$ | OH | =O | H |
| 19 | H | OCH$_3$ | H | α H β ethyl | H |

*This is also the number of the Example in wich the compound is demonstrated.
**CH$_3$—CO—

The $R_2$ and $R_3$ substituted compounds of this invention can be prepared using one or more of the following reactions:

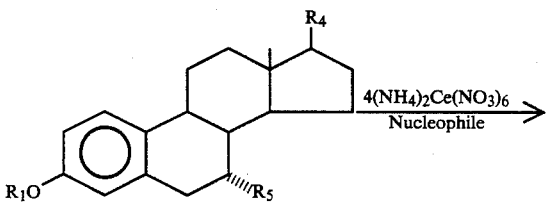

In this reaction, $R_1$, $R_4$ and $R_5$ can be as defined above. A nitrate $R_2$ group can be inserted by the use of ceric ammonium nitrate. Halo $R_2$'s can be inserted by the use of ceric ammonium nitrate together with a halo-containing nucleophile such as lithium chloride or lithium bromide or the like. An alkoxy $R_2$ can be inserted by the use of ceric ammonium nitrite together with the alkanol corresponding to the alkoxy. The $R_3$ group will be OH if no alkanol is present and can be alkoxy if alkanol is present.

This reaction is generally carried out using excess ceric ammonium nitrate, i.e., a 1.5 to 10 molar excess. When forming compounds having a nitrate $R_2$ group the starting steroid and the ceric ammonium nitrate are mixed, generally in a polar solvent, especially 80–100% acetic acid and stirred at low to moderate temperatures such as 5° to 40° C. for from about 1 hour to about 24 hours. When adding halo $R_2$'s an excess (2 to 20 molar) of halo nucleophile is used. It is added together with the ceric ammonium nitrate. When adding alkoxy $R_2$'s, the polar solvent such as acetic acid solvent may at least in part be replaced by the alkanol.

In all cases excess water is to be avoided and an inert gas cap over the reaction vessel is preferred.

Alternatively, one can use the 9,11Δ steroids as starting material in the reaction

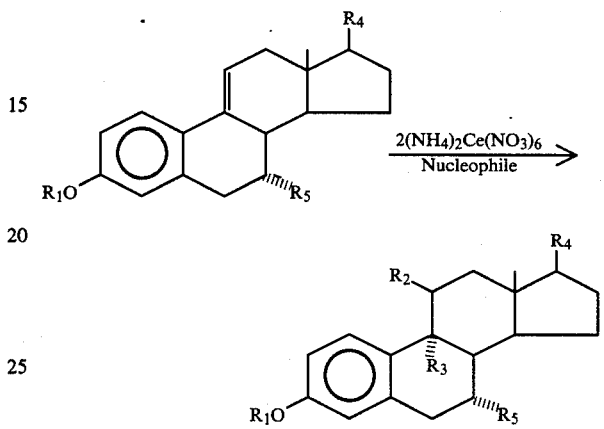

In this reaction, less ceric ammonium nitrate (2 moles rather than 4) is consumed. The same reaction conditions as above can be used.

The compounds of this invention wherein $R_3$ is hydrogen (i.e., the 11-substituted materials) can be formed from the above-described 9,11-substituted materials by treatment with silane followed by reduction with boron trifluoride etherate. The silane employed may be a trialkyl silane such as trimethyl silane or triethyl silane. Generally a molar excess of silane and boron trifluoride etherate are employed. This reaction is generally carried out in dry solvent, such as dry methylene chloride, dry ethylene chloride or the like under an inert atmosphere initially at low temperatures such as −15° to 10° and thereafter at moderate temperatures such as 10° to 50° C.

$R_2$—ONO$_2$ groups can be converted to —OH's using zinc in the reaction

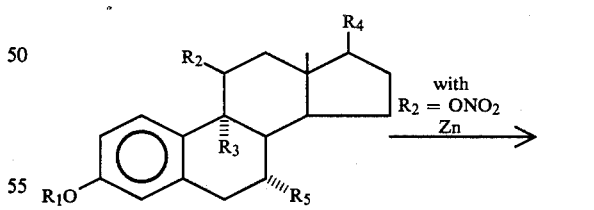

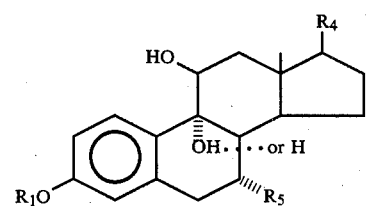

This reaction is generally carried out using an excess of powdered zinc in a polar solvent such as glacial acetic acid. This reaction is preferably conducted under an inert atmosphere and can be completed at temperatures of from 10° to 50° C. in from 0.1 to about 2 hours.

A carbonyl $R_4$ substituent can be converted to an alpha hydrogen and a beta hydroxyl by reduction with excess sodium borohydride. This reaction can be carried out in a dry oxyhydrocarbon solvent such as anhydrous lower alkanols or the like. Suitable reaction conditions are from 5 minutes to 30 minutes at temperatures of from 10° to 50° C., preferably 20° to 50° C.

Other changes to $R_4$ groups can be carried out. For example, a Grignard-type reaction can be carried out to react the $R_4$ carbonyl with an alkyl, alkenyl, or alkynyl magnesium bromide thereby converting the $R_4$ to the corresponding alpha alkyl, alkenyl or alkynyl, beta hydroxy $R_4$. This reaction can be carried out by gradually adding the carbonyl oxygen-containing steroid to a stirred solution of the magnesium bromide reagent at low temperature such as $-10°$ to 20° C. for a time of from a few hours (for example 5) to several days. Water should be excluded from this reaction. THF or another aprotic solvent can be used as the reaction medium for this reaction.

After any of these reactions the products or intermediates can be collected and worked up by methods known in the art, including, without limitation, extraction, chromatography such as high pressure liquid chromatography, thin layer chromatography, paper chromatography, and liquid chromatography, precipitation, cyrstallization and the like.

The invention will be further described by the following examples. These are provided only to illustrate embodiments of the invention and are not to be construed as limitations on the invention's scope.

EXAMPLE 1

3,9α,11β-Trihydroxy-7α-methyl-estra-1,3,5(10)-trien-17-one 3-acetate 11-nitrate ester (1)

To a stirred solution of 20 g (64.3 mM) of 7α-methylestrone acetate in 400 ml of 90% acetic acid under a nitrogen atmosphere, 140 g (266 mM) of ceric ammonium nitrate was added. The reaction mixture was stirred for 6 hr at room temperature and then added to 2 l of water. The precipitated products were extracted into 750 ml of ether, and the aqueous phase was extracted with an additional 750 ml of ether. The ether extracts were combined and washed—three times with 750 ml portions of water, once with 750 ml of a 5% sodium bicarbonate solution, and once with 750 ml of water. The ether solution was dried over sodium sulfate, and then the ether was removed at reduced pressure to afford 24.8 g of residue. Crystallization from ether gave 10.5 g of 1. An analytical sample was prepared by recrystallization from ether; mp, 184°–186°.

Anal. high-resolution mass spec. for $C_{21}H_{25}O_5$ (M—$NO_2$): Calcd. 357.1702; Found: 357.1712

EXAMPLE 2

Treatment of Δ9,11-7α-methylestrone acetate with two equivalents of ceric ammonium nitrate gave 1 identical to the material obtained above.

EXAMPLE 3

17α-Ethynyl-3,9α,11β-17β-tetrahydroxy-estra-1,3,5(10)-trien 3,17-Diacetate 11-Nitrate Ester (3)

The procedure of Example 1 was repeated but employing ethynyl estradiol acetate (1.0 g) as the starting material. This gave 300 mg of 3 on crystallization from ether. An analytical sample was prepared by recrystallization from ether; mp 173°–175°.

Anal. high resolution mass spec. for $C_{24}H_{27}NO_8$: Calcd. 357.2066. Found: 357.2103

EXAMPLE 4

3,9α,11β-Trihydroxy-19-norpregna-1,3,5(10)-trien 3-Acetate 11-Nitrate Ester (4)

The procedure of Example 1 was repeated but employing 1 g of 3-hydroxy-19 norpregna-1,3,5(10)-trien 3-acetate. This gave, on crystallization from ether-petroleum-ether, 350 mg of 4. An analytical sample was prepared by recrystallization from ether; mp 177°–179°.

EXAMPLE 5

3,9α,11β-Trihydroxy-7α-methyl-19-norpregna-1,3,5(10)-trien 3-Acetate 11-Nitrate Ester (5)

The procedure of Example 1 was repeated but employing 7α-methyl-19-norpregna-1,3,5(10)-trien. This gave, on separation by preparative tlc, 59 mg of 5. An analytical sample was prepared by recrystallization from ether; mp 140°–143°.

Anal. high resolution mass spec. for $C_{23}H_{31}O_4$(M-$NO_2$): Calcd. for 371.222; Found: 371.2231.

EXAMPLE 6

3,11β-Dihydroxy-7α-methyl-estra-1,3,5(10)-trien-17-one 3-acetate 11-nitrate ester (6)

To a stirred solution of 10.5 g (25.5 mM) of 1 in 400 ml of dry methylene chloride under a nitrogen atmosphere at salt-ice bath temperature, 10 g (76.5 mM) of triethyl silane followed by 26.8 ml of boron trifluoride etherate were added. The reaction mixture was stirred for 1 hr and then warmed to room temperature. The methylene chloride solution was washed three times with 150-ml portions of a 10% potassium carbonate solution and once with 150 ml of water; then it was dried over sodium sulfate. The methylene chloride was removed at reduced pressure, and crystallization from ether gave 5.75 g of 6. An analytical sample was prepared by recrystallization from ether; mp, 195°–196°.

Anal. Calcd. for $C_{21}H_{25}NO_6$ C, 65.10; H, 6.50; N, 3.62. Found: C, 65.11; H, 6.58; N, 3.57.

EXAMPLE 7

3,11β-Dihydroxy-estra-1,3,5(10)-trien-17-one 3-Acetate 11-Nitrate Ester (7)

Treatment of 5 g of estrone acetate with ceric ammonium nitrate by the procedure described in Example 1 gave, on crystallization from ether, 2.1 g of the intermediate ester 3,9α,11β-Trihydroxy-estra-1,3,5(10)trien-17-one 3-Acetate 11-Nitrate Ester.

By the procedures used in Example 3, 310 mg of the ester just prepared gave, on crystallization from ether, 150 mg of pure 8, mp 190°–192°.

Anal. Calcd. for $C_{20}H_{23}NO_6$: C, 64.33; H, 6.21; N, 3.75. Found: C, 64.09; H, 5.95; N, 3.62.

EXAMPLE 8

3,11β,17β-Trihydroxy-7α-methyl-estra-1,3,5(10)-trien 11 Nitrate ester (8)

To a stirred solution of 100 mg of 6 from Example 6 in 12 ml of methanol 48 mg of sodium borohydride was added. The reaction mixture was stirred for 15 min then added to 75 ml of water. The product was extracted into 75 ml of ether and the etheral solution was washed with water then dried over sodium sulfate. The ether was removed at reduced pressure to give 100 mg of residue. An analytical sample was prepared by crystallization from methylene chloride: mp 179°–182°.

Anal. GC mass spec for $C_{19}H_{25}NO_5$: Calcd. for 347; Found 347.

EXAMPLES 9 AND 10

3,9α,11β-Trihydroxy-estra-1,3,5(10)-trien-17-one 3-Acetate 9α-Methy ether 11-Nitrate ester (9) and 3,9α,11β-trihydroxy-estra 1,3,5(10)trien-17-one 3-Acetate 9,11-Dimethyl ether (10)

To a stirred solution of 310 mg of Δ9,11-estrone acetate in 10 ml of methanol under a nitrogen atmosphere 1.1 g of ceric ammonium nitrate was added. The reaction mixture was stirred for 45 min at room temperature then added to 100 ml of water. The reaction products were extracted into 100 ml of ether, then the etheral solution was washed twice with water then dried over sodium sulfate. The solvent was removed at reduced pressure to give 370 mg of residue. Separation by preparative thin layer chromatography gave 160 mg of 9 and 160 mg of 10.

Anal. 9 GC mass spec. for $C_{22}H_{28}O_5$: Calcd. for 362; Found: 362.

Anal. 10 GC mass spec. for $C_{21}H_{25}NO_6$: Calcd. 403; Found: 403.

EXAMPLE 11

11β-Chloro-3-hydroxy-estra-1,3,5(10)-trien-17-one 3-Acetate (11)

To a stirred solution of 1.0 g (3.3 mM) of Δ9,11-estrone acetate and 1.25 g (30 mM) of lithium chloride in 30 ml of 90% acetic acid under nitrogen was added 3.8 g (6.8 mM) of ceric ammonium nitrate. The reaction mixture was stirred for 3 hr and then added to 250 ml of ice water. The product was extracted into 100 ml of ether. The ether solution was washed three times with water, twice with 5% $NaHCO_3$, and once with water and then dried over sodium sulfate. The solvent was removed at reduced pressure to afford 1.2 g of residue. Crystallization from ether gave 530 mg of the intermediate 11β-Chloro-3,9α-dihydroxy-estra-1,3,5(10)-trien-17-one 3-Acetate. An analytical sample was prepared by recrystallization from ether.

Anal. GC mass spec. for $C_{20}H_{23}ClO_4$: Calcd. for 362; Found: 362.

By the procedure used in Example 6, reaction of 362 mg of the intermediate gave, on crystallization from ether 190 mg of 11: mp 187°–190°.

Anal. GC mass spec. for $C_{20}H_{23}ClO_3$: Calcd. for 346; Found: 346.

EXAMPLE 12

17α-Ethylnyl-7α-methyl-estra-1,3,5(10)-trien-3,9α,11β-tetraol (12)

To a stirred solution of 10 mM of ethynyl magnesium bromide in 25 ml of THF at 0° under nitrogen was added 360 mg of 3,9α,11β-trihydroxy-7-α-methyl-estra-1,3,5(10)-trien-17-one 3-acetate in 8 ml of THF dropwise over 10 min. The reaction mixture was warmed to room temperature and then stirred for 18 hr. A solution of 1 ml of saturated $NH_4Cl$ was added and stirring was continued for 15 min. Then 100 ml of ether was added. The ether solution was washed three times with water and then dried over sodium sulfate. Removal of the solvent at reduced pressure gave 400 mg of residue. Fractionation by preparative tlc (benzene-50% ether SiGF) gave 100 mg of 12.

Anal. high resolution mass spec. for $C_{21}H_{24}O_3$: Calcd. for 324.1725. Found: 324.1754.

EXAMPLE 13

3,9α,11β-Trihydroxy-7α-methyl-estra-1,3,5(10)-trien-17-one 3-Acetate (13)

To a stirred solution of 2.3 g of the nitrate ester of Example 1 in 100 ml of glacial acetic acid under nitrogen was added 9.2 g of powdered zinc. The reaction mixture was stirred for 1 hr. Then the zinc suspension was added to 800 ml of ice water and the acetic acid was neutralized with 2N sodium hydroxide. The product was extracted into 400 ml of ether, and the ether solution was washed three times with water and then dried over sodium sulfate. The solvent was removed at reduced pressure to afford 1.4 g of residue. Crystallization from ether gave 361 mg of 13. An analytical sample was prepared by recrystallization from ether; mp 188°–190°.

Anal. high resolution mass spec. for $C_{21}H_{26}O_5$: Calcd. for 358.1780. Found: 358,1776.

EXAMPLE 14

3,11β-Dihydroxy-7α-methyl-estra-1,3,5(10)-trien-17-one 3-acetate (14)

To a stirred solution of 5.2 g of the nitrate ester of Example 6 in 150 ml of glacial acetic acid under a nitrogen atmosphere, 7.5 g of zinc dust was added. The reaction mixture was stirred for 1 hr at room temperature and then filtered through celite, and the filter cake was washed with 100 ml of glacial acetic acid. Most of the acetic acid was removed at reduced pressure; then 300 ml of water was added, and precipitated product was extracted into 500 ml of ether. The ether solution was washed twice with 150 ml of water, once with 150 ml of a 5% sodium bicarbonate solution, and with 150 ml of water; then it was dried over sodium sulfate. The ether was removed at reduced pressure to afford 4.5 g of crude 14. Crystallization from ether gave 2.3 g of pure 14. Preparative tlc (SiGF-benzene-25% ether) gave an additional 1.4 g of pure 14. An analytical sample was prepared by recrystallization from methylene chloride-ether; mp, 130°132°.

Anal. Calcd. for $C_{21}H_{26}O_4$: C, 73.66; H, 7.65. Found: C, 73.84; H, 7.66.

EXAMPLE 15

3,11β-Dihydroxy-estra-1,3,5(10)-trien-17-one 3-Acetate 11-Methy ether (15)

The process of Example 6 is repeated substituting as feed stock, 150 mg of the nitrate ester produced in Example 9. This gave, on crystallization from ether, 100 mg of 15: mp 180°–182°.

Anal. GC mass spec. for $C_{22}H_{26}O_4$: Calcd. for 342; Found: 342.

EXAMPLE ≠

3,9α,11β-Trihydroxy-estra-1,3,5(10)-trien-17-one 3,11-Dimethyl ether (16)

To a slurry of 284 mg of estrone methyl ether in 20 ml of methanol under a nitrogen atmosphere a solution of 3.3 g of ceric ammonium nitrate in 30 ml of methanol was added dropwise over 3 hr. The reaction mixture was added to 150 ml of water and the products were extracted into 100 ml of ether. The ether solution was washed with water then dried over sodium sulfate. The ether was removed at reduced pressure to give 300 mg of residue. Separation by preparative thin layer chromatography gave 130 mg of 16. An analytical sample was prepared by crystallization from ether: mp 191°–194°.

Anal. GC mass spec. for $C_{20}H_{26}O_4$: Calcd. for 330; Found: 330.

EXAMPLE 17

11β-Chloroethynylestradiol 3-Methyl Ether (17)

Precursor Preparation

2-Chloro-1,1,2-trifluorotriethylamine 1-chloro-1,2,2-trifluoroethylene was bubbled into 50.0 g of triethylamine for 8 hr at −5° to −10°. The reaction was the distilled under reduced pressure to yield 61 g of product, bp 35°/6 mm (lit[10] bp 32°–33°/6 mm). The 2-chloro-1,1,2-trifluorotriethylamine was stored in vials under nitrogen, wrapped in aluminum foil and placed in a desicator.

11β-Chloroestrone 3-Methyl Ether

To a solution of 3.0 g of 11α-hydyroxyestrone 3-methyl ether in 120 ml of dry THF at 0°–5° (ice-water bath) was added 0.7 g of dry lithium chloride (dried in a desiccator at 80° under vacuum at 1.0 mm for 18 hr) and 2.25 ml of the above-prepared haloamine. The reaction was stirred at this temperature for 18 hr. Tlc indicated that the reaction had not gone to completion; therefore, an additional 0.2 ml of the haloamine reagent and 0.07 g of lithium chloride were added. After being stirred for an additional hr at 0°–5°, the reaction was poured into ether and water. The ether phase was separated and washed with water. The ether solution was dried over sodium sulfate and evaporated at reduced pressure to yield 2.70 g of crude 21. The crude product was purified by hplc to yield 0.750 g of 21, which was recrystallized from methanol to yield 0.550 g; mp 129.5–130.0.

Anal. high resolution mass spec calcd for $C_{19}H_{23}O_2Cl$: calcd 318.1389; found 318.1410.

GRIGNARD REAGENT

Dry acetylene was prepared by passing the gas through two traps (one cooled with dry-ice/acetone); and then through a column of KOH pellets, Drierite, and KOH pellets. The dry acetylene was bubbled into 25.0 ml of dry THF at 0°–5° for 1.5 hr. To the acetylene solution was added dropwise 0.766 ml of 3.0 ethyl magnesium bromide. The reaction was stirred for an additional 0.20 hr at 0°–5°.

THE DESIRED PRODUCT (17)

To the Grignard reagent reaction solution was then added 0.18 g of the 11β-chloroestrone-3-methyl ether in 8.0 ml of dry THF. The reaction was allowed to warm to room temperature and stirring was continued for 18 hr. To quench the reaction, 5 ml of saturated $NH_4Cl$ was slowly added. The THF was evaporated at reduced pressure and the residue was dissolved in ether. The ether solution was washed with saturated $NH_4Cl$, dried over $Na_2SO_4$ and evaporated at reduced pressure to yield 0.172 g of crude product. The crude product was chromatographed on 20 g of silica gel and eluted with benzene-7% ether to afford 0.063 g of pure 17; mp 173°–174°.

Anal. high resolution mass spec calcd for $C_{21}H_{25}O_2Cl$: calcd 344.1543; found 344.1555.

EXAMPLE 18

Compound 18 was prepared using the general techniques taught herein.

EXAMPLE 19

Compound 19 was prepared using the general techniques taught herein.

EXAMPLE 20

3,9 alpha,11 beta-Trihydoxy-estra-1,3,5(10)trien-17-one 3-Acetate 11-Nitrate Ester (20)

The process of Example 1 is repeated but using 5 g of strone acetate as starting material. This gave, on crystallization from ether, 2.1 g of 20. An analytical sample was prepared by recrystallization from ether. The sample (m.p. 183°–184°) had spectral properties consistent with the structure of 20.

BIOLOGICAL ACTIVITY

The compounds of this invention exhibit significant estrogenic activity and postcoital contraceptive activity. This is demonstrated in the following tests.

ORAL ESTROGENIC ACTIVITY

The estrogenic acitivity was determined using immature female rats ovariectomized at 21 days of age. Treatment was by oral administration for 4 days, beginning on the day of ovariectomy. Animals were autopsied on the day following the last administration of test compound. Vaginal smears were obtained from animals that had open vaginas at the time of autopsy. The endpoints for comparison with a standard estrogen will be the increase in uterin weight and cornification of vaginal smears. (The test compounds were diluted with a 0.5% Carboxymethyl cellulose suspension.)

ORAL POSTCOITAL ACTIVITY

Oral postcoital activity was determined using adult cycling female rats, obtained from the Holtzman Rat Company, were selected in the proestrous phase of the cyle. Treatment began on the day of proestrus. Each female was caged overnight with two adult males. The find of sperm in the vaginal smear the following morning was used as evidence of insemination. Treatment was continued for a total of 8 days. The rats were sacrificed on the day following the last treatment, and the number of implantation sites and the number of corpora lutea were counted. The test material was administered parenterally (sc or im or orally by intubation).

SUBCUTANEOUS ESTROGENIC ACTIVITY

Immature, 18-day-old rats are assigned randomly to groups of 5 to 10. Treatment by S.C. injection is started on the day the animals arrive and continues once daily for 4 days. On day 5, vaginal smears are obtained, and uteri—carefully dissected between precise areas between the cervix and the oviduct—are stripped of fat and connective tissue and then weighed on a torsion balance. Fluid in uteri is expressed before weighing. Body weights of rats are recorded on the first day and at autopsy.

Comparison of the semilog dose-response curves of 3 to 4 dose levels of an active test compound with those of compounds of known activity (e.g., estrone administered s.c. or ethinyl estradiol given orally) helps determine whether the estrogen is strong, weak, or impeded and may give some indication of potential antiestrogenic activity.

Contraceptive activity test

The activities so determined are listed in Table 2.

TABLE 2

| Compound | Estrogenic Activity (Oral) | Contraceptive Activity -(Oral) | Estrogenic Activity relative to Estradiol (Subcutaneous) |
|---|---|---|---|
| Standard (Ethynyl Estradiol) | 100 | 100 | 1000 |
| 1. | | | 34 |
| 2. | | | |
| 3. | 531 | 5000 | |
| 4. | 228 | 4000 | |
| 5. | 780 | | |
| 6. | 696 | 4000 | 7472 |
| 7. | 400 | | |
| 8. | 1400 | | |
| 9. | 8 | | |
| 10. | 5 | | |
| 11. | | | 7–12 |
| 12. | 445 | 400 | |
| 13. | 1 | | |
| 14. | | | 26–69 |
| 15. | 60 | | |
| 16. | | | |
| 17. | 300 | >100 | |
| 18. | 22 | 200 | |
| 19. | 37 | >2000 | |
| 20. | | | 40 |

As can be seen from these results, several of the compounds provide estrogenic activities that are as much as 7, 14 and even 26 times as great as ethynyl estradiol, itself one of the most potent estrogens. Similarly, compounds of this invention can exhibit postcoital infertility activity 40 and 50 times as high as ethynyl estradiol. This points to significantly lowered use levels which could in turn reduce side effects.

The compounds of this invention can be administered to humans or other mammals by any of the accepted modes of administration for steroidal agents. These methods include oral, parenteral, suppositories, topical and the like. The compounds can be administered alone or as part of a combination product—such as with a progestin or the like.

Depending on the intended mode of administration, the compositions used may be in the form of solid, semisolid or liquid dosage forms, such as, for example, injectables, tablets, suppositories, pills, capsules, powders, liquids, suspensions, or the like, preferably in unit dosage forms suitable for single administration of precise dosages. The compositions will include a conventional pharmaceutical carrier or excipient and an active compound of the invention and, in addition, may include other medicinal agents, pharmaceutical agents, carriers, adjuvants, etc. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, sucrose, magnesium, carbonate, and the like. Such compositions take the form of solutions, suspensions, tablets, pills, capsules, powders, sustained release formulations and the like.

The compounds of the invention as defined above may be formulated as suppositories using, for example, polyalkylene glycols, for example, propylene glycol, as the carrier.

Liquid pharmaceutically administerable compositions particularly for parenteral administration (generally characterized by injection—subcutaneously, intramuscularly or intravenously) can be prepared by dissolving, dispersing, etc. a compound of the invention and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) adequate to achieve the desired estrogenic or contraceptive effect in the subject being treated.

The amount of active compound administered will, of course, be dependent on the activity of the compound, the effect desired and the view of the attending physician. As guidelines, conventional oral estradiol pills and tablets may contain from 0.5 to about 2 mg of active material, while a dose of injectable estradiol may be from about 1 to about 10 mg of the active material. Oral ethynyl estradiol tablets usually contain in the range of from 0.01 to 1 mg of the active material. Oral contraceptives employing ethynyl estradiol generally contain from about 0.02 to about 0.1 mg of ethynyl estradiol. In view of the activities demonstrated with compounds of this invention one could obtain desired responses with from as little as 0.0002 mg of active material to as much as 5 or 10 mg. The following nonlimiting representative product formulations further illustrate the use of the present materials in pharmaceutical composition.

FORMULATION A

Estrogenic Tablet

| Ingredients | Quantity, g |
|---|---|
| Compound of Example 8 | 0.005 |
| Cornstarch | 40 |
| Lactose | 58 |
| Magnesium stearate | 2 |

The above materials are blended in a lab scale v-blender and hand pressed into 100 mg tablets each of which administers a unit dose of 0.005 mg of the estrogenic compound of example 8.

FORMULATION B

Estrogenic Capsule

| Ingredients | Quantity, g |
|---|---|
| Compound of Example 5 | 0.05 |
| Lactose (spray dried) | 198 |
| Magnesium stearate | 2 |

The above materials are mixed to give a free flowing powder. Hard shell gelatin capsules are filled with 200 mg of the above mixture to achieve a unit dosage form for 0.05 mg estrogen therapy.

FORMULATION C

Estrogenic Vaginal Cream

A vaginal cream is formulated by admixing 0.15 mg/g of final product of Example 12 in a cream base made up of glycerin, mineral oil, glycerol monostearate, polyethylene glycol ether complex of fatty acids, cetyl alcohol, lanolin. When one cc of this product is administered an estrogenic response is achieved:

FORMULATION D

Androgen-Estrogen Tablets

| Ingredients | Quantity, g |
| --- | --- |
| Methyl testosterone | 1.25 |
| Compound 6 of Example 6 | 0.10 |
| Cornstarch | 75 |
| Lactose | 168.75 |
| Magnesium stearate | 5.0 |

The above materials are intimately mixed and formed into 1000 250 mg tablets each of which delivers 1.25 mg of androgen and 0.10 mg of estrogen.

FORMULATION E

Oral Contraceptive Tablet

| Ingredient | Quantity, g |
| --- | --- |
| Compound 6 of Example 6 | 0.001 |
| Norgestrol progestogen | 5.0 |
| Lactose | 95 |
| Cornstarch | 145 |
| Magnesium stearate | 5 |

The above ingredients are mixed and formed into 250 mg tablets which when administered to a female exhibit contraceptive activity.

FORMULATION F

Oral Contraceptive

| Ingredient | Quantity, g |
| --- | --- |
| Compound 3 of Example 3 | 0.01 g |
| Lactose | 100 |
| Cornstarch | 145 |
| Magnesium stearate | 5 |

The above ingredients are mixed and formed into 250 mg tablets which when administered to a female human exhibit postcoital contraceptive activity.

FORMULATION G

Topical Formulation

| Ingredients | Quantity, g |
| --- | --- |
| Active compound 12 of Example 12 | 0.002 |
| Span 60 | 2 |
| Tween 60 | 2 |
| Mineral Oil | 5 |
| Petrolatum | 10 |
| Methyl paraben | 0.15 |
| Propyl paraben | 0.05 |
| BHA (butylated hydroxy anisole) | 0.01 |

| Ingredients | Quantity, g |
| --- | --- |
| Water q.s. | 100 |

All of the above ingredients, except water, are combined and heated to 60° C. with stirring. A sufficient quantity of water at 60° C. is then added with vigorous stirring to emulsify the ingredients, and water then added q.s. 100 g.

What is claimed is:

1. A compound of the formula

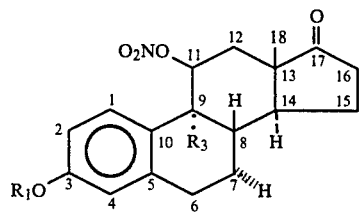

wherein $R_1$ is selected from the group consisting of hydrogen, lower alkyl, cycloalkyl and lower acyl; and $R_3$ is lower alkoxyl.

2. The compound of claim 1 wherein $R_1$ is acetyl.

3. A compound of the formula

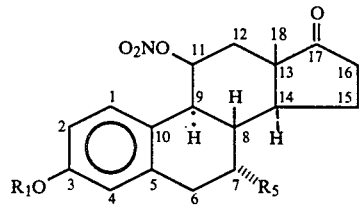

wherein $R_1$ is selected from the group consisting of hydrogen, lower alkyl, cycloalkyl and lower acyl; and $R_5$ is selected from the group consisting of lower alkyl and hydrogen.

4. The compound of claim 3 having the formula

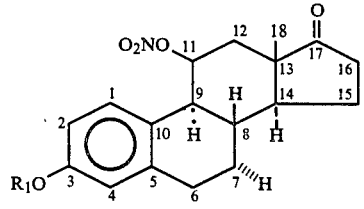

wherein $R_1$ is selected from the group consisting of hydrogen, lower alkyl, cycloalkyl and lower acyl.

5. The compound of claim 4 having the formula

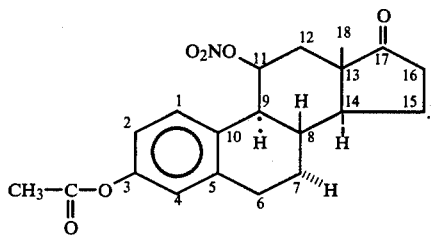

6. The compound of claim 3 wherein $R_5$ is a lower alkyl.

7. The compound of claim 6 having the formula

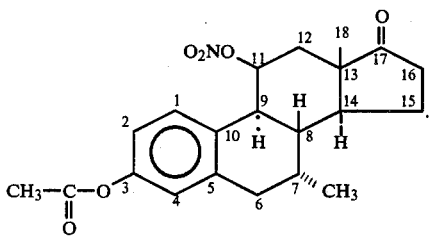

8. A compound of the formula

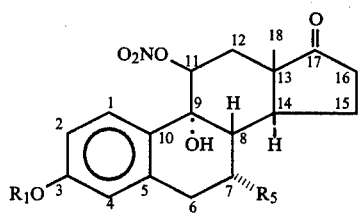

wherein
$R_1$ is selected from the group consisting of hydrogen, lower alkyl, cycloalkyl and lower acyl; and
$R_5$ is a lower alkyl.

9. A compound of the formula

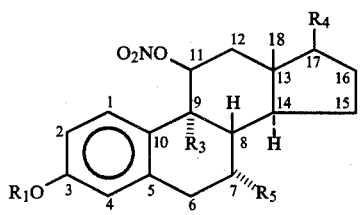

wherein
$R_1$ is selected from the group consisting of hydrogen, lower alkyl, cycloalkyl and lower acyl;
$R_3$ is selected from the group consisting of hydrogen, hydroxyl and lower alkoxy;
$R_4$ is a pair of substituents the α one of which being selected from hydrogen and lower alkynyl, and the β one of which being selected from alkanoic acid esters, lower alkyl and hydroxyl; and
$R_5$ is selected from the group consisting of lower alkyl and hydrogen, subject to the proviso that if $R_4$ is an α hydroxyl and a β alkanoic acid ester or hydrogen, then $R_5$ must be a lower alkyl.

10. A compound of the formula

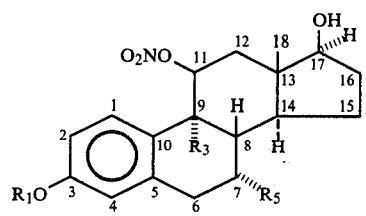

wherein
$R_1$ is selected from the group consisting of hydrogen, lower alkyl, cycloalkyl, and lower acyl;
$R_3$ is selected from the group consisting of hydrogen, hydroxyl, and lower alkoxy; and
$R_5$ is a lower alkyl.

11. The compound of claim 10 having the formula

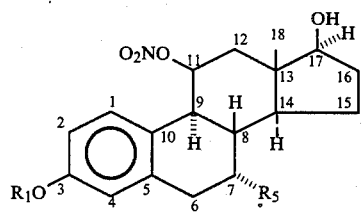

wherein
$R_1$ is selected from the group consisting of hydrogen, lower alkyl, cycloalkyl, and lower acyl; and
$R_5$ is a lower alkyl.

12. The compound of claim 11 having the formula

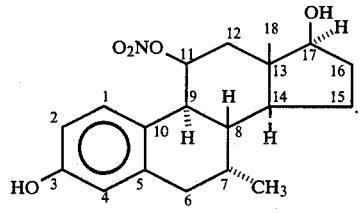

13. A compound of claim 9 of the formula wherein
$R_1$ is selected from the group consisting of hydrogen, lower alkyl, cycloalkyl and lower acyl;
$R_4$ is a pair of substitutents, the α one of which being a lower alkynyl and the β one of which being a hydroxyl; and
$R_5$ is a lower alkyl.

14. A compound of claim 13 of the formula

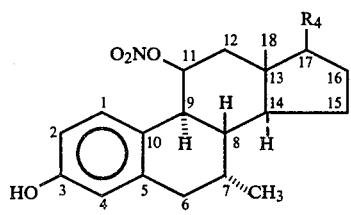

wherein
R₄ is a pair of substituents the α one of which being a lower alkynyl and the β one of which being a hydroxyl.

15. The compound of claim 14 having the formula

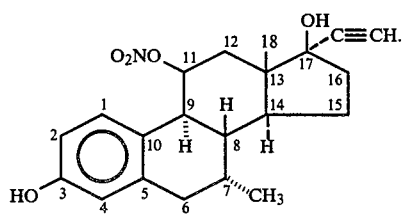

16. The compound of claim 9 wherein R₄ is an α hydrogen and a α lower alkyl and R₃ is hydroxyl.

17. The compound of claim 16 wherein R₅ is a lower alkyl.

18. The compound of claim 16 wherein R₅ is hydrogen.

19. The compound of claim 18 having the formula

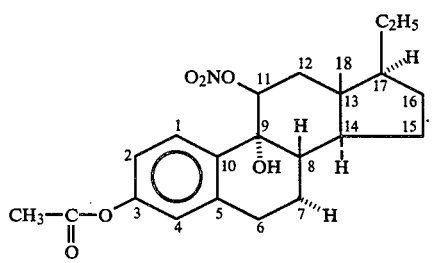

20. The compound of claim 9 wherein R₄ is an α alkynyl and a β lower alkanoic acid ester.

21. The compound of claim 16 having the formula

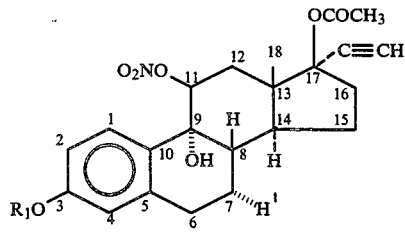

wherein R₁ is selected from the group consisting of hydrogen, lower alkyl, cycloalkyl and lower acyl.

22. The compound of claim 21 having the formula

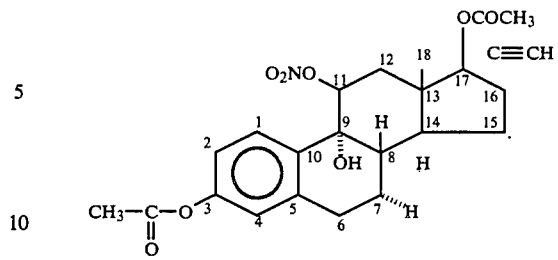

23. A pharmaceutical composition useful for producing an estrogenic effect in a female mammal which comprises an effective estrogenic amount of a compound of claim 3 in admixture with a pharmaceutically acceptable excipient.

24. A pharmaceutical composition useful for producing a contraceptive effect in a female mammal which comprises an effective contraceptive amount of a compound of claim 3 in admixture with a pharmaceutically acceptable excipient.

25. A method of treating a female mammal to achieve an estrogenic effect therein which comprises administering to said mammal an effective estrogenic amount of the pharmaceutical composition of claim 23.

26. A method of treating a female mammal to achieve a contraceptive effect therein which comprises administering to said mammal an effective contraceptive amount of the pharmaceutical composition of claim 24.

27. A pharmaceutical composition useful for producing an estrogenic effect in a female mammal which comprises an effective estrogenic amount of a compound of claim 10 in admixture with a pharmaceutically acceptable excipient.

28. A pharmaceutical composition useful for producing a contraceptive effect in a female mammal which comprises an effective contraceptive amount of a compound of claim 10 in admixture with a pharmaceutically acceptable excipient.

29. A pharmaceutical composition useful for producing an estrogenic effect in a female mammal which comprises an effective estrogenic amount of a compound of claim 12 in admixture with a pharmaceutically acceptable excipient.

30. A pharmaceutical composition useful for producing a contraceptive effect in a female mammal which comprises an effective contraceptive amount of a compound of claim 12 in admixture with a pharmaceutically acceptable excipient.

31. A pharmaceutical composition useful for producing an estrogenic effect in a female mammal which comprises an effective estrogenic amount of a compound of claim 13 in admixture with a pharmaceutically acceptable excipient.

32. A pharmaceutical composition useful for producing a contraceptive effect in a female mammal which comprises an effective contraceptive amount of a compound of claim 13 in admixture with a pharmaceutically acceptable excipient.

33. A pharmaceutical composition useful for producing an estrogenic effect in a female mammal which comprises an effective estrogenic amount of a compound of claim 15 in admixture with a pharmaceutically acceptable excipient.

34. A pharmaceutical composition useful for producing a contraceptive effect in a female mammal which comprises an effective contraceptive amount of a compound of claim 15 in admixture with a pharmaceutically acceptable excipient.

* * * * *